United States Patent [19]

Haas

[11] Patent Number: 4,948,367

[45] Date of Patent: Aug. 14, 1990

[54] ORTHODONTIC ACCESSORIES AND METHOD OF APPLYING THE SAME

[75] Inventor: Martin Haas, Stow, Ohio

[73] Assignee: Summit Orthodontic Services, Inc., Cuyahoga Falls, Ohio

[21] Appl. No.: 208,113

[22] Filed: Jun. 17, 1988

[51] Int. Cl.$^5$ .............................................. A61C 3/00
[52] U.S. Cl. .......................................... 433/9; 433/24
[58] Field of Search .......................... 433/8, 9, 17, 24; 40/638

[56] References Cited

U.S. PATENT DOCUMENTS

| | | | |
|---|---|---|---|
| 3,250,002 | 5/1966 | Collito | 433/9 X |
| 3,294,611 | 12/1966 | Vomela | 40/299 X |
| 3,504,438 | 4/1970 | Wittman et al. | 433/8 |
| 3,745,653 | 7/1973 | Cohl | 433/24 |
| 3,822,492 | 7/1974 | Crawley | 40/299 |
| 4,094,068 | 6/1978 | Schinhammer | 433/9 |
| 4,204,325 | 5/1980 | Kaelble | 433/9 |
| 4,626,209 | 12/1986 | Tsai et al. | 433/9 |
| 4,695,251 | 9/1987 | Randklev | 433/8 |
| 4,752,221 | 6/1988 | Hanson et al. | 433/9 |

Primary Examiner—John J. Wilson
Assistant Examiner—Nicholas D. Lucchesi
Attorney, Agent, or Firm—Reese Taylor

[57] ABSTRACT

An orthodontic accessory comprising an attachment contiguous with a base and a layer of pressure sensitive adhesive applied to the base to interact with the tooth and a removable backing protecting the adhesive. The removable backing is scored or perforated so that a relatively small portion can be initially removed for initial placement of the accessory and is also optionally oversized with respect to the size of the base to facilitate removal. The method of treatment includes the steps of preliminarily removing a portion of the backing and preliminarily positioning the accessory on the tooth, followed by removal of the remainder of the backing and finally positioning the accessory on the tooth and applying force to effect a bind between the accessory and the tooth.

1 Claim, 1 Drawing Sheet

ORTHODONTIC ACCESSORIES AND METHOD OF APPLYING THE SAME

BACKGROUND OF THE INVENTION

This invention relates, in general, to orthodontic accessories and treatment methods and relates, in particular, to orthodontic accessories having a pressure sensitive adhesive thereon permitting improvements in the use of such accessories in orthodontic treatment. This invention also relates to a method of applying these novel orthodontic accessories to the teeth of patients.

DESCRIPTION OF THE PRIOR ART

In conventional methods of orthodontic treatment, orthodontic devices are bound to metallic bands which are, in turn, mounted onto the tooth. In general, a bracket would be welded to the band. An arch wire would then be connected to the bracket thereby permitting force to be applied directly to the tooth so as to properly position the tooth within the dental arch. This conventional process, however, gives rise to several problems, including patient discomfort, gingival irritation, decalcificiation and difficulty in alignment.

It is known in the art to avoid such problems by bonding the bracket directly to the tooth, thus obviating the need for the band. Bandless brackets generally have at least two structural features. One is that the bracket body has grooves which are suitably configured for receiving an arch wire. The other is a bracket base which provides support for the bracket body. The base also provides a surface which can be affixed or attached to the tooth.

Direct attachment of such orthodontic devices to the teeth creates several problems. One problem is that an orthodontic accessory which is affixed directly to the tooth with an adhesive is difficult to correctly position. Moreover, inasmuch as the adhesives commonly used are generally quick curing, initial correct placement is required. If correct placement is not initially obtained, removal of the attachment becomes necessary.

This removal is disadvantageous to the patient because it creates discomfort and further increases the time that is required for the treatment. Alleviation of patient discomfort must be a prime objective for any orthodontic work.

Such removal is also deleterious to the tooth surface as it results in damage to the tooth enamel.

Another problem with conventional direct attachment is that an orthodontic accessory which is directly bound to the tooth with an adhesive may have insufficient bonding strength.

It will also be noted that orthodontic accessories, and in particular brackets, are usually made of stainless steel, plastic or ceramic type materials. Plastic materials are generally more aesthetically pleasing, yet present other disadvantages, i.e., discoloration, splintering and distortion. With use of stainless steel accessories, especially in the case of bandless brackets, it is known to configure the base with slots, mesh or various types of indents. The indents are necessary because of the difficulty in bonding the stainless steel, plastic or ceramic type bases to the tooth. The indents or mesh provide mechanical retention and serve to form a physical lock between the bracket base or various auxiliary bases, adhesive and tooth surface. The manufacture of these accessories, however, is cumbersome and costly.

It is also known to spray the base with a molten, corrosion-resistant titanium carbide powder, as is set forth in Tsai U.S. Pat. No. 4,626,209. This process, however, is both laborious and cost ineffective.

Furthermore, in general, adhesives are untidy because, in use, they may spill or splash on objects other than the tooth or the accessory to be mounted thereto. When these other objects include the patient, or parts of the patient, discomfort or unpleasantry is enhanced. Moreover, with use of some adhesives, a reaction can occur when the adhesive is inadvertently placed on, or permitted on, surfaces other than the tooth surfaces, namely, parts of the patient's mouth.

Additionally, use of conventional adhesives results in damage to the tooth surface, as described in Randklev U.S. Pat. No. 4,695,251. As set forth therein, while orthodontic brackets which can be applied directly to the tooth have become popular because they are simpler to apply to the teeth than the old style bands, the use of such brackets and other orthodontic accessories can lead to tooth enamel damage. Such damage is the result of preparation of the tooth for use with the adhesive which includes etching the enamel which results in loss of enamel, opening the pores of the enamel and the loss of the natural sheen of enamel. Further damage may occur during the actual application of the adhesive and also the removal of the bracket base or auxiliary base at the termination of the treatment process. For example, it is presently known that tooth enamel has been removed when removing bracket bases.

It is also known that after bonded bases have been removed from the tooth, there is present on the tooth surface a residue of the adhesive or bonding medium used. This residue must be removed from the tooth surface by scraping, grinding, polishing or the use of some type of abrasive or chipping medium. This is very time consuming, can be injurious to tooth enamel, is uncomfortable to the patient, and is every expensive from the personnel standpoint. Most importantly, this process could lead to cross infections between patients and personnel in the event of incomplete sterilization due to the sharp cutting nature of residue removal devices such as instruments, wheels and razor sharp carbide and diamond burrs.

Therefore, it is a primary object of the present invention to provide an orthodontic accessory which does not suffer from the foregoing disadvantages.

SUMMARY OF THE INVENTION

It has been found that the aforementioned objective can be achieved by providing an orthodontic accessory which comprises an orthodontic attachment having a base suitably configured to be affixed directly to the tooth surface. A pressure sensitive adhesive is then applied to this base. Further, the adhesive is provided with a protective backing or release material which can be removed prior to use.

It has been found that the orthodontic accessory of the present invention can be sufficiently bonded to the tooth surface, yet provide improved positioning capabilities. In affixing the accessory to the tooth, the accessory may be positioned, or even repositioned, with ease. Furthermore, the accessory may be easily removed after the duration of the orthodontic treatment without severe damage to the tooth surface.

It has been found that the orthodontic accessory of the present invention alleviates problems heretofore experienced with conventional adhesives. In particular, the untidiness of the application of the adhesive to the tooth and accessory in the treatment environment is obviated. Moreover, the orthodontic accessories of the present invention are both clean and safe, thus providing benefits to the user as well as the treating orthodontist.

It has also been found that application of the orthodontic accessory can be further facilitated by perforating the release material so that only a small amount can be removed initially and the accessory can be temporarily positioned. In this fashion, if the initial positioning is incorrect, only an insignificant amount, if any, of adhesive residue needs to be removed from the tooth.

Finally, it has been found that these and other objects of the present invention which will be apparent from the description to follow are accomplished by the means hereinafter described and claimed and illustrated in the accompanying drawings.

OF THE DRAWINGS

BRIEF DESCRIPTION OF THE PREFERRED EMBODIMENTS

It will be noted that the present invention is directed toward both an apparatus and the method for employing the same. In particular, the present invention is directed to an orthodontic accessory having a pressure sensitive adhesive thereon and the method of using this accessory in orthodontic treatment.

Figure 1:
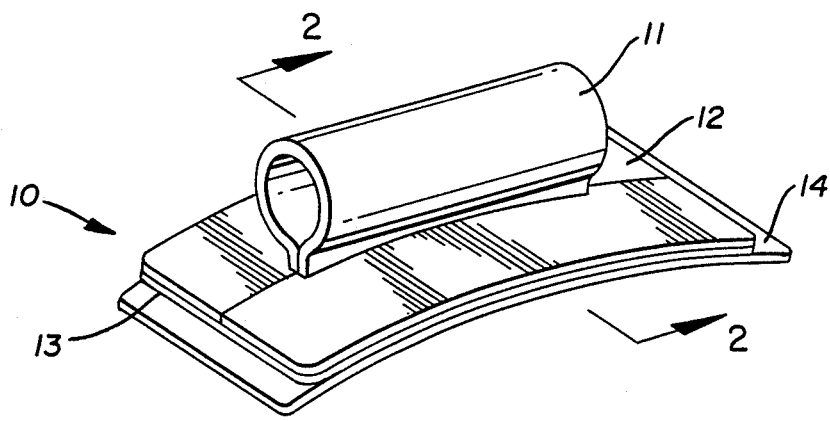
FIG. 1 is an elevational view of an exemplary orthodontic accessory of the present invention.
Figure 2:
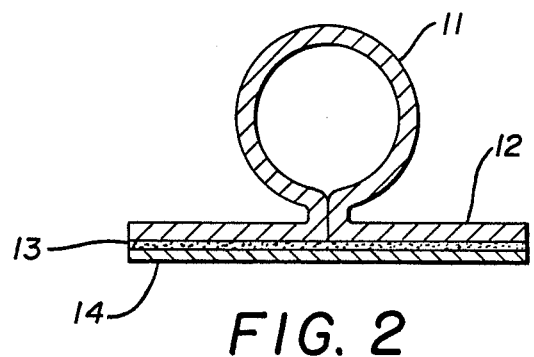
FIG. 2 is a sectional view of the exemplary accessory of FIG. 1 along the line 1—1 thereof.

The orthodontic accessory 10 of the present invention, as shown generally in FIG. 1, comprises an orthodontic attachment 11 and a base portion 12. Attachment 11 comprises a buccal tube in the drawing; however, numerous attachments are within the spirit of the present invention, including but not limited to, brackets, buccal tubes, hooks, lugs, eyelets, cleats, plain bases, sheaths, springs, caps, stops and various other auxiliaries used in the practice of orthodontics. It should be appreciated that the foregoing are merely exemplary of the types of attachments which may be employed in the orthodontic accessories of the present invention and do not serve to limit the invention. In general, any orthodontic auxiliary having use in some aspect of orthodontic treatment may be attachment 11 of the accessory 10 of the present invention.

The base portion 12 of the accessory is contiguous with attachment 11 and, in general, is located below the attachment. Preferably, base 12 is dimensional to the tooth upon which it is rest. Therefore, base 12 may be suitably configured so as to be placed about the tooth.

Base 12 may be comprised of any conventional material, including stainless steel, ceramic or plastic. An orthodontic accessory comprised of a stainless steel material is often preferred to ceramic or plastic, but the present invention is not intended to be limited by the material of the accessory.

A pressure sensitive adhesive 13 is applied to base 12 during manufacture. Pressure sensitive adhesive 13 is applied to the entire surface of base 12 and is of a minimal thickness. A typical presure sensitive adhesive is MACbond Rubber S.P.R. #IB1111 which is sold by Morgan Adhesives Company, Stow, Ohio. MACbond Rubber S.P.R. #IB1111 has tenacious holding power in excess of intended use requirements. Upon initial placement, 80% to 85% of the total holding power is achieved. Within 15 to 30 minutes, the normal body temperature will increase the holding capacity of the adhesive to 100%. The particular adhesive mentioned is effective in temperatures ranging from 40° to 150° F. The total contemplated thickness of the adhesive is 0.0045. This thickness is ideal in that it not only insures proper bonding, but it also affords a slight amount of cushioning between the attachment (bracket) base 12 and the tooth surface. This cushioning leads to increased patient comfort. It should be noted that, while the foregoing adhesive is preferred, the subject invention is not limited to such a material, but rather is limited only by the scope of the attached claims.

Adhesive 13 is provided with a protective backing 14 or release material. Backing 14 may be of any known material, such as film or coated paper, and is releasably attached to pressure sensitive adhesive 13, but does not deleteriously affect the adhesiveness of the same. That is, upon removal of the backing 14, adhesive 13 is activated such that the orthodontic accessory may be affixed to the tooth surface by means of the adhesive.

Figure 3:
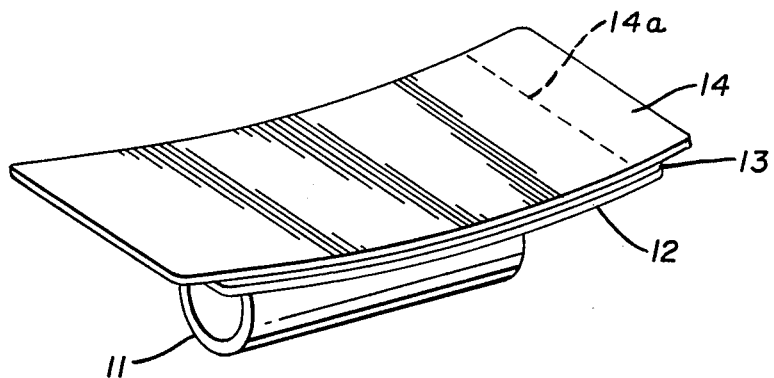
FIG. 3 is a perspective view of the exemplary accessory of FIG. 1.

It will also be seen, with reference to FIG. 3 of the drawings, that the release material 14 has two additional features which facilitate use of the accessory 10.

First, the material 14 is perforated or scored as at 14a so that a relatively small area of adhesive may be selectively exposed. This enables the accessory to be preliminarily positioned while engaging the tooth with only a relatively small amount of adhesive. Therefore, if repositioning should be required, only the relatively small amount of adhesive needs to be removed from the tooth. This feature also makes it easier to handle the accessory since most of the adhesive 13 is covered until final positioning.

Second, the release material 14 is optionally oversized with respect to the base 12. This facilitates removal since the portion thereof which extends beyond the basee can be readily grasped for removal.

In use of the orthodontic accessory of the present invention, one first selects the attachment 11 which is desired or needed. Attachment 11, of course, is, or can be, designed according to the present invention in that it has a base portion 12, as described hereinabove. The desired location within the dental arch for this attachment is then determined. Orthodontic accessory 10 may then be placed within the patient's mouth for initial placement purposes. This is, orthodontic accessory 10 may be placed upon the tooth surface without intended to affix accessory 10 to the tooth surface for sizing and/or other preliminary observations. Pressure sensitive adhesive 13 is prevented from contacting the tooth surface due to the presence of protective backing 14.

Once the proper location and proper attachment has been determined, the orthodontic accessory 10 of the present invention may be affixed directly to the tooth surface. This is accomplished by first removing a predetermined minute portion of protective backing 14 with the assistance of score line 14a from base 12 of the orthodontic accessory 10. This removal may be done manually or with the assistance of a removal device, such as tweezers. Once the small portion of protective backing 14 is removed from base 12 of orthodontic accessory 10, some of pressure sensitive adhesive 13 is exposed. The orthodontic accessory may be inserted within the patient's mouth at the proper location which has heretofore been determined.

If the location is then determined to be correct, the remainder of release material 14 may be removed. Once this has been accomplished, the accessory is affixed to the tooth surface through the application of force on the accessoary in the direction of the tooth surface, or in other words, by simply pressing it in place.

If it is determined tht the initial positioning of the accessory 10 is improper due to the nature of pressure sensitive adhesive 13, accessory 10 may be easily removed from its location and repositioned as necessary. This may be done simply by applying force upon accessory 10 in a direction opposed to the tooth surface to peel it off the tooth. Accessory 10 may then be repositioned in its appropriate spot. Again, once the proper location is finally determined, orthodontic accessory 10 may be finally applied by removing the remaining portion of the protective backing and, again, through the application of force, directed toward the tooth surface.

This final application differs from previous applications in that orthodontic accessory 10 is not removed thereafter. The amount of force applied in the direction of the tooth surface upon the orthodontic accessory in this final application may be greater than used in the previous applications. However, this is not required.

It should be appreciated that orthodontic accessory 10 of the present invention and method for applying the same provide beneficial improvements over the prior art. In addition to the obvious advantages in positioning, handling, safety and cleanliness, the subject invention is cost-effective, as they can be easily produced. Moreover, the orthodontic accessories of the present invention can include virtually any orthodontic auxiliary and thus provides versatility heretobefore unavailable.

While a full and complete description of the invention has been set forth in accordance with the dictates of the Patent Statutes, it should be understood that modifications can be resorted to without departing from the spirit hereof or the scope of the appended claims.

What is claimed is:

1. A method of orthodontic treatment for affixing an orthodontic accessory directly to the teeth of the patient, comprising the steps of:
    (a) determining the proper location of an orthodontic accessory;
    (b) obtaining said orthodontic accessory having an orthodontic attachment, said attachment being contiguous with a base, said base carrying a pressure sensitive adhesive protected on one side by a removable backing;
    (c) removing a portion of said removable backing from said orthodontic accessory thereby exposing said pressure sensitive adhesive;
    (d) positioning said orthodontic accessory in mating juxtaposition with a tooth of the patient;
    (e) applying force to said orthodontic accessory in the direction of the tooth to which the accessory is juxtaposed, thereby effecting a bind between said accessory and the tooth;
    (f) repositioning the orthodontic accessory to achieve optimum placement by applying force to the orthodontic accessory in a direction away from the tooth;
    (g) adjusting the location of the accessory; and
    (h) removing the remaining protective backing and applying force to the accessory in the direction of the tooth at the accessory's new location.

* * * * *

UNITED STATES PATENT AND TRADEMARK OFFICE
CERTIFICATE OF CORRECTION

PATENT NO. : 4,948,367

DATED : August 14, 1990

INVENTOR(S) : Martin Haas

It is certified that error appears in the above-identified patent and that said Letters Patent is hereby corrected as shown below:

In Column 1, Line 26, delete "decalcificiation" and substitute therefor --decalcification--.

In Column 2, Line 38, delete "every" and substitute therefor --very--.

In Column 3, Line 55, delete "is rest" and substitute therefor --is to rest--.

In Column 4, Line 41, delete "basee" and substitute therefor --base--.

In Column 4, Line 50, delete "This" and substitute therefor --That--.

In Column 4, Line 51, delete "intended" and substitute therefor --intending--.

In Column 4, Line 67, delete "may be" and substitute therefor --may then be--.

UNITED STATES PATENT AND TRADEMARK OFFICE
CERTIFICATE OF CORRECTION

PATENT NO. : 4,948,367

DATED : August 14, 1990

INVENTOR(S) : Martin Haas

It is certified that error appears in the above-identified patent and that said Letters Patent is hereby corrected as shown below:

In Column 5, Line 7, delete "accessoary" and substitute therefor --accessory--.

In Column 5, Line 9, delete "tht" and substitute therefor --that--.

Signed and Sealed this

Fifth Day of November, 1991

Attest:

HARRY F. MANBECK, JR.

Attesting Officer

Commissioner of Patents and Trademarks